(12) United States Patent
Wang et al.

(10) Patent No.: US 8,574,837 B2
(45) Date of Patent: Nov. 5, 2013

(54) SYSTEM FOR SCREENING AGONISTS/ANTAGONISTS OF CELLULAR SIGNALING PATHWAYS

(75) Inventors: Yu Wang, Madison, WI (US); Andrew P. McMahon, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 157 days.

(21) Appl. No.: 13/142,438

(22) PCT Filed: Dec. 29, 2009

(86) PCT No.: PCT/US2009/069640
§ 371 (c)(1),
(2), (4) Date: Sep. 9, 2011

(87) PCT Pub. No.: WO2010/078290
PCT Pub. Date: Jul. 8, 2010

(65) Prior Publication Data
US 2011/0319286 A1    Dec. 29, 2011

Related U.S. Application Data

(60) Provisional application No. 61/141,035, filed on Dec. 29, 2008.

(51) Int. Cl.
*C12Q 1/68* (2006.01)
(52) U.S. Cl.
USPC ............ 435/6.1; 435/325; 435/375; 536/23.4
(58) Field of Classification Search
None
See application file for complete search history.

(56) References Cited

U.S. PATENT DOCUMENTS 7,060,450 B1    6/2006 Tabin et al.
2006/0247419 A1    11/2006 Dahl et al.

FOREIGN PATENT DOCUMENTS

EP    1199564    4/2002
WO    2008/060478    5/2008

*Primary Examiner* — Jim Ketter
(74) *Attorney, Agent, or Firm* — David S. Resnick; Nixon Peabody LLP

(57) ABSTRACT

The present invention identifies a method for investigating the response of a cell membrane-associated protein in a living cell to a drug by labeling the protein with a visual marker, and also selectively labeling the membrane portion of the protein with another visual marker, such that upon exposure of the cell to a stimulus, the translocation of the cell membrane-associated protein may be observed directly.

15 Claims, 8 Drawing Sheets

| Name | Structure | $EC_{50}/IC_{50}$ | Reference |
|---|---|---|---|
| SAG | 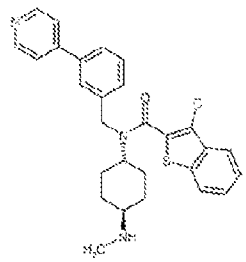 | 3nM | Lauth et al., 2007; Rohatgi et al., 2007 |
| purmorphamine | 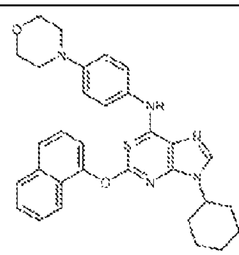 | 1000nM | Sinha & Chen, 2006 |
| 20-OHC | 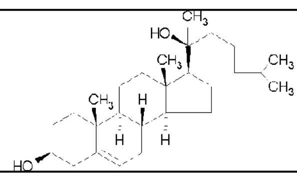 | 100nM | Williams et al., 2003 |
| cyclopamine | 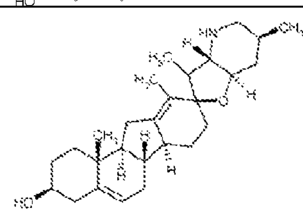 | 300nM | Kimura et al., 2008 |
| SANT-1 | 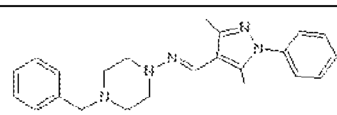 | 20nM | Lauth et al., 2007 |
| SANT-2 | 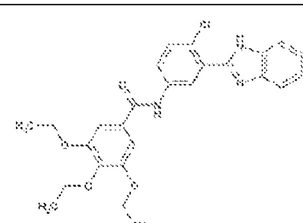 | 30nM | Lauth et al., 2007 |
| GANT61 | 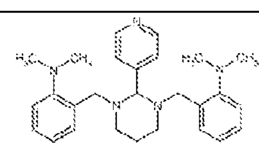 | 5000nM | Romer et al., 2004 |

Figure 9

SYSTEM FOR SCREENING AGONISTS/ANTAGONISTS OF CELLULAR SIGNALING PATHWAYS

CROSS REFERENCE TO RELATED APPLICATIONS

This application is a 35 U.S.C. §371 National Phase Entry Application of International Application No. PCT/US2009/069640 filed Dec. 29, 2009, which designates the United States and which claims benefit under 35 U.S.C. §119(e) of U.S. Provisional Application No. 61/141,035, filed Dec. 29, 2008, the contents of which are incorporated herein by reference in their entirety.

GOVERNMENT SUPPORT

This invention was made with government support under grant NS033642 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on May 2, 2013, is named 002806-064422-US_SequenceListing.txt and is 1,776 bytes in size.

FIELD OF THE INVENTION

The present invention relates to molecular and cellular biology, and provides a system for high throughput screening of agonists and/or antagonists of cellular signaling pathways in living cells. A particular embodiment provides for monitoring and high throughput screening of the selective translocation of intracellular Smoothened to and from the primary cilium in response to Hedgehog pathway modulation.

BACKGROUND

Cellular signaling is crucial in several different developmental pathways and adult homeostatic processes. For example, in cellular signaling, tight regulation of Hedgehog (Hh) signaling is essential in building and maintaining functional systems in the body. Hh signaling is implicated in many human diseases, notably several neurodegenerative diseases and a variety of cancers including basal cell carcinoma, medulloblastoma, rhabdomyosarcoma, pancreatic cancer, prostate cancer, and lung cancer.

The identification of mutations in Hh pathway components has stimulated the identification of over a dozen Hh agonists and antagonists that fall into chemically distinct classes. Most of these compounds target the protein Smoothened (Smo). In the mammalian signaling pathway, the binding of a Hh ligand to its receptor Patched 1 (Ptch1), relieves Ptch1-mediated inhibition of Smo, a second trans-membrane protein. The activation of Smo then triggers an intracellular signal transduction cascade that culminates in Gli-dependent (glioma-associated oncogene-dependent) transcriptional activities. Hence, a mechanistic understanding of Smo and how it interacts with potential signaling modulators is important for the development of effective drugs and therapies for Hh-related diseases. Current drug screening methods for Hh signaling pathway agonists and antagonists use downstream transcriptional activity as readout, which is indirect and does not distinguish between different Smo translocation mechanisms. In addition, previous methods have limited information depth, specificity, and statistical robustness Thus, there remains a need for additional methods, including high throughput methods, for screening modulators of Smo, Hh and other cellular signaling pathways.

SUMMARY

The embodiments of the present invention provide a system for screening intracellular signaling modulators. More specifically, the present invention provides for screening, including high throughput screening, for modulators that effect cilial translocation of Hh signaling pathway components such as Smo. This high content screen methodology is directly based on drug-Smo interactions to screen drug candidates for Hh-related diseases by visualizing Smo and tracing its cellular localization in Hh-responsive cells. Using the present invention, one can distinguish different classes of antagonists that inhibit Hh activity with different mechanisms early in drug development. Specificity is high in this well-defined assay, providing deeper and broader information including cell morphology and compound toxicity. The inventive method also shows higher level of statistical robustness because thousands of cells can be analyzed readily. This new method provides better guidance for ramifications among drug candidates from early stage and provides a paradigm shift of screening strategy in drug development for intracellular signaling.

Hence, an object of the present invention provides for a novel system and methodology for screening drug candidates for Hh-related diseases based, for example, on Smo interactions. In an embodiment of the present invention, Smo is visualized and its cellular localization traced in Hh-responsive cells. Reagents that regulate Smo activity are identified by scoring directly the change of cilial localization of Smo. This inventive approach allows researchers to distinguish different classes of antagonists that inhibit Hh activity with different mechanisms, providing crucial information for drug screening strategy and clinical development.

More specifically, Smo, a seven pass transmembrane protein, is essential for transduction of a Hedgehog (Hh) signal from the cell membrane. Mammalian Smo translocates to the primary cilium in response to Sonic Hedgehog (Shh) ligand-mediated signaling. Smo is also the principle therapeutic target for several candidate drugs in the treatment of Hh-related diseases. A mechanistic understanding of Smo translocation and its interactions with drug candidates is pivotal to understanding Hh signaling; and for designing, developing, and applying successful drugs.

The present invention also provides for a system in which Smo is dual-labeled with green fluorescent protein (GFP), and/or with a 12-amino-acid-tag (A1) whose recognition by an enzymatic process enables the post-translational labeling of Smo in the cell membrane of the living cell. In particular, an aspect of the present invention provides for short tag phosphopantetheinyl transferase (PPTase) labeling, a versatile approach in examining membrane protein synthesis, movement, and accumulation within a living cell. For example, PPTase labeling provides effective multi-color labeling of a novel protein, A1::Smo::GFP, yielding the first insights into the dynamics of Smo turnover in the primary cilium. Alternative dual labeling constructs include EGFP::Smo and Inversin::tagRFPT. This important methodology extends the reach of molecular imaging studies, and supports high throughput screening of drug (e.g., small molecules or agents) candidates that impact cell membrane proteins that translocate in response to stimuli. For example, cells may be grown and tested in a 384-well format, and visualization and scoring may be completely automated.

An embodiment of the present invention provides for a method for screening a drug affect on the Hedgehog (Hh) signaling pathway comprising the steps of culturing a first population and second population of cells, wherein both populations express a A::Smoothened::Fluorescent Protein construct (A::Smo::FP), and wherein A is a fragment of an acyl carrier protein that suffices for post-translational phosphopantetheinylation of A::Smo::FP protein; labeling both the first and second cell populations with a fluorophore using AcpS; contacting the first cell population with a Hh ligand or empty vehicle; contacting the second cell population with a Hh ligand and a drug or a drug only; observing the cilial translocation of said A::Smo::FP in the first cell population and in the second cell population by visualizing the FP and fluorophore; comparing the cilial translocation of said A::Smo::FP in the first cell population with the second cell population; wherein a difference in cilial translocation of said A::Smo::FP in the first cell population and the second cell population provides an indication of whether said drug affects the Hh signaling pathway. The FP may be GFP, Yellow Fluoresent Protein (YFP), or another fluorescent protein.

An aspect of the invention provides for a cell culture system comprising a population of cells that expresses a reporter construct comprising A::Smo::FP, and wherein A is a fragment of an acyl carrier protein that suffices for post-translational phosphopantetheinylation in a living cell, Smo is Smoothened protein, and FP is a fluorescent protein. A related aspect provides for a method of identifying a drug that affects a Hh signaling pathway comprising contacting this cell culture system with a candidate drug and detecting an effect on the reporter construct as compared with a culture system not contacted with the drug, wherein a difference is indicative of a drug that affects a Hh signaling pathway. This method may be automated.

This system allows the simultaneous visualization of all cellular Smo and, more specifically, the cell membrane restricted subpopulation. For example, the approach taught herein demonstrates that cyclopamine, a widely used Hh antagonist, induces a cilial translocation of Smo similar to that reported for Shh ligand and several Hh agonists. Cyclopamine promotes Smo accumulation in the primary cilium, suggesting a possible issue with cyclopamine action wherein Smo that has accumulated in the primary cilium may lead to a strong, prolonged stimulation after drug removal. In contrast, other antagonists abrogate the Shh-induced cilial translocation of Smo. The majority of cilial-localized Smo originates from an intracellular source and may traffic to the primary cilium through an intraflagellar transport (IFT) pathway.

DESCRIPTION OF THE DRAWINGS

FIG. 1A shows that a 12-amino-acid-A1-tag (A1) (SEQ ID NO: 2) was added to the extracellular N-terminus of human Smo and GFP was fused to the intracellular C-terminus. FIG. 1B shows holo-(acyl carrier protein) synthase (AcpS) enzyme transfers a fluorophore to the serine in the A1 tag (marked in 1A) through a phosphopantetheinyl (Ppant) group in the CoA-fluorophore substrate, thereby labeling A1::Smo::GFP with a specific fluorophore.

FIG. 9 is a summary of Hh pathway modulators explored in the system of the present invention.

DETAILED DESCRIPTION

Figure 1A:
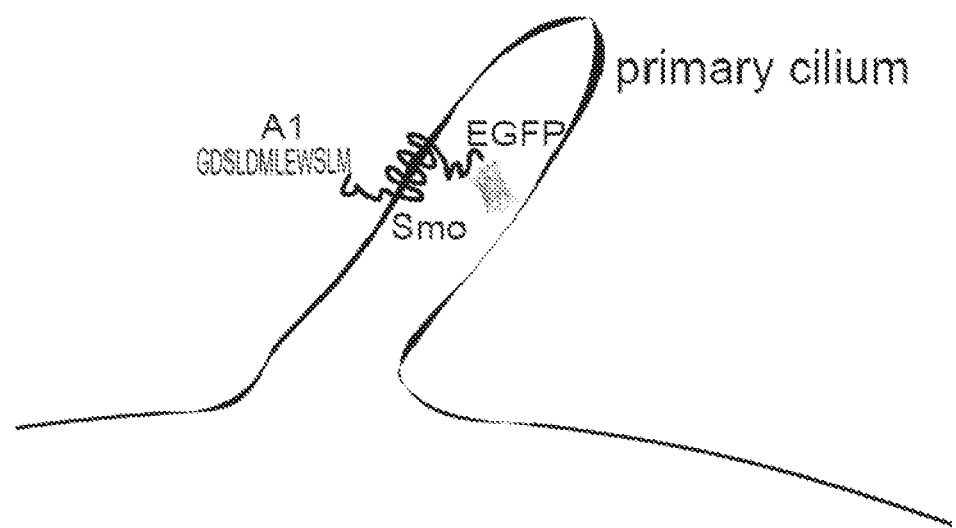
FIGS. 1A-1B depict the generation of a dual labeled A1::Smo::GFP reporter construct.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Hedgehog (Hh) signaling is one of the central pathways governing development and also linked to a number of human diseases, notably several neurodegenerative diseases and a variety of cancers (Rubin & de Sauvage, 5 Nat. Rev. Drug Discov. 1026-33 (2006); Dellovade et al., 29 Ann. Rev. Neurosci. 539-63 (2006)) A tight regulation of Hh signaling is essential in building and maintaining functional systems in the body (see McMahon et al., 53 Curr. Top Devel. Biol. 1-114 (2003)). Recently, the discovery of a generic role of Hh signaling in supporting tumor growth promises huge potential of using Hh antagonists in conjunct therapy for cancers. Yauch et al., 455 Nature 406-10 (2008)). In both academia and industry, there has been enormous interest in mechanistically dissecting and regulating this pathway over the past two decades. An embodiment of the present invention analyzes Hedgehog (Hh) signaling, which is involved in multiple developmental pathways and several adult homeostatic processes.

In the mammalian signaling pathway, the binding of a Hh ligand to its receptor Patched 1 (Ptch1) relieves Ptch1-mediated inhibition of a second trans-membrane protein Smoothened (Smo). Smo, a GPCR protein, is essential for transduction of Hh signal across the cell membrane. Activation of Smo triggers an intracellular signal transduction cascade that culminates in Gli-dependent, transcriptional activities. Genetic ablation of Smo leads to a complete loss of Hh responsiveness in target cells (Zhang et al., 105 Cell 781-92. (2001)). Conversly, activating mutations in Smo result in a hyper-stimulation of Hh signaling (Xie et al., 391 Nature 90-92 (1998)). Currently, almost all small molecule regulators of the Hh signaling pathway interact directly with Smo, which makes the protein the principle therapeutic target in the pathway. The translocation of Smo to the primary cilium marks the initiation of cellular response to Hh stimulation (Corbit et al., 437 nature 1018-21 (2005)). Given the significance of Smo as a "popular" therapeutic target, better mechanistic understanding of Smo translocation and its interactions with drug candidates is pivotal to drug design, development and applications.

As noted, Hh signaling is linked to a number of human diseases: notably several neurodegenerative diseases and a variety of cancers (see Rubin & de Sauvage, 2006). The identification of mutations in Hh pathway components has stimulated the identification of over a dozen Hh agonists and antagonists that fall into chemically distinct classes (Id.; Bijlsma, et al., 4 PLoS Biol e232 (2006); Chen et al., 99 P.N.A.S. 14071-76 (2002); Corcoran & Scott, 103 P.N.A.S. 8408-13 (2006); Frank-Kamenetsky et al., 1 J. Biol. 10 (2002); Lauth et al., 104 P.N.A.S. 8455-60 (2007); Rohatgi et al., 317 Science 372-76 (2007); Sinha & Chen, 2 Nat. Chem. Biol. 29-30 (2006); Williams et al., 100 P.N.A.S. 4616-21 (2003)). Smo is the target protein for most of these compounds, even though a mechanistic understanding of Smo and how it interacts with these compounds is not thoroughly understood. Thus, the mechanisms of Hh antagonist activities are of particular interest given their potential use in cancer therapy (Rubin & de Sauvage, 2006; Kimura et al., 13 Cancer Cell 249-60 (2008); Romer et al., 6 Cancer Cell 229-40 (2004)).

A widely studied Hh antagonist is cyclopamine, a natural product derived from corn lily (Taipale et al., 406 Nature 1005-09 (2000)). Further, a number of cyclopamine derivatives have been described that offer improved pharmacological and inhibitory properties (Tremblay et al., 51 J. Med. Chem. 6646-49 (2008)). The present invention has revealed, as shown herein, that cyclopamine induces a cilial translocation of Smo similar to translocations stimulated by Shh ligand and several Hh agonists. In contrast, other antagonists abrogate Shh-induced cilial translocation of Smo. The finding that cyclopamine promotes Smo accumulation at the primary cilium suggests a possible issue with cyclopamine action: where the Smo that has accumulated in the primary cilium may lead to a strong, prolonged stimulation after drug removal. Thus, the mechanistic differences among antagonists provides crucial insight in the choice of one drug versus another for clinical development, and promises a better outcome for drug development as information is obtained at an earlier stage of therapeutic development.

More specifically, the primary cilium has emerged as a central organelle essential for Hh signal transduction in mammalian systems (see Eggenschwiler & Anderson, 23 Ann. Rev. Cell Devel. Biol. 345-73 (2007)). Multiple components of the Hh pathway localize to the primary cilium or its basal body, including Shh (Rohatgi et al., 2007; Chamberlain et al., 135 Devel. 1097-106 (2008)), Ptch1 (Rohatgi et al., 2007), Smo (id.; Corbit et al., 437 Nature 1018-21 (2005); Han et al., 11 Nat. Neurosci. 277-84 (2008); Kiprilov et al., 180 J. Cell Biol. 897-904 (2008); Kovacs et al., 320 Science 1777-81 (2008); May et al., 287 Devel. Biol. 378-89 (2005); Tran et al., 40 Nat. Genet. 403-10 (2008)), suppressor of Fused (suFU, a key negative regulator of Gli activity), and Gli transcription factors (Kiprilov et al., 2008); Tran et al., 2008; Haycraft et al., 1 PLoS Genet. e53 (2005). In the absence of Shh, Ptch1 is enriched in the primary cilium of cultured mammalian cells; its cilial localization is lost following engagement with Shh ligand (Rohatgi et al., 2007).

Conversely, Smo becomes enriched on the primary cilium upon treatment with Shh or several pathway stimulators including the small molecule agonist, Ag1.3 (also known as SAG) (Chen et al., 2002; Frank-Kamenetsky et al., 2002; Rohatgi et al., 2007) and 20α-hydroxycholesterol (20-OHC), a candidate small molecule for communication between Ptch1 and Smo (Corcoran & Scott, 2006; Rohatgi et al., 2007). Interestingly, a tryptophan-to-leucine mutation in the seventh trans-membrane helix bundle of Smo generates a dominant-active form (SmoA1), that constitutively localizes to the primary cilium (Corbit et al., 2005; Han et al., 2008). Downstream of Smo, suFU and Gli proteins concentrate in or about the primary cilium (Kiprilov et al., 2008; Tran et al., 2008; Haycraft et al., 2005). Further, their normal function depends on the intact primary cilium (May et al., 2005; Haycraft et al., 2005; Huangfu & Anderson, 102 P.N.A.S. USA 11325-30 (2005); Liu et al., 132 Devel. 3103-11 (2005); Caspary et al., 12 Devel. Cell 767-78 (2007). The present invention allows for visualization of how Hh pathway components move in and out of the primary cilium, and how the cilial localization modulates their activities.

Intraflagellar transport (IFT) is required for the assembly and maintenance of the primary cilium. Membrane proteins are thought to be transported within the primary cilium via IFT particles. These particles consist of sixteen IFT proteins that form two multi-protein IFT complexes: A and B. The movement of IFT particles from the base to the tip of cilium is powered by anterograde kinesin-II motor complexes, while retrograde transport is driven by dynein motor complexes (Rosenbaum & Witman, 3 Nat. Rev. Mol. Cell. Biol. 813-25 (2002)). A correlation between Hh signaling and the primary cilium was made when mouse mutations removing IFT function were shown to lead to a failure of cilial formation resulting in a spectrum of Hh-related phenotypes (May et al., 2005; Haycraft et al., 2005; Huangfu & Anderson, 2005; Liu et al., 2005; Huangfu et al., 426 Nature 83-87 (2003)). These phenotypes may result as an indirect consequence of ciliary abnormalities or more directly if IFT trafficking is itself a component of Hh signaling.

The present invention harnesses short tag phosphopantetheinyltransferase (PPTase) labeling: a versatile tool to investigate membrane proteins. The work presented herein demonstrates the efficacy and efficiency of the PPTase labeling technology in examining cell membrane protein accumulation and movement in a living cell. For example, PPTase labeling enables effective dual-color labeling of the recombinant reporter protein A1::Smo::GFP, providing the first insights into the dynamics of Smo turnover in the primary cilium. Further, the 'built-in' spatial resolution of the system, a property of the cell exclusion of CoA substrates, allows the study of trafficking mechanisms (such as Smo trafficking) because it distinguishes cell membrane populations from intracellular pools.

Further regarding the PPTase labeling, this is achieved by adding a genetically encoded fragment of an acyl carrier protein to a membrane-associated portion of a recombinant membrane protein. After transduction into a cell population, holo-(acyl carrier protein) synthase (AcpS) enzyme is used to transfer a fluorophore to the serine in the tag through a phosphopantetheinyl (Ppant) group in the CoA-fluorophore substrate, thus allowing post-translational modification of the reporter protein. For example, when live, transformed cells can be incubated with AcpS and Texas Red, and the portion of the cell membrane protein associated with the membrane becomes labeled with the fluor (see Examples, below). Additionally, the recombinant membrane protein may include another visual marker such as a fluorescent protein (e.g., GFP), that may be visible upon translation regardless of post translational modification of membrane tags. In this way, the same protein can be observed by direct visualization of the dual fluors, and translocation of the protein from the membrane followed.

To dynamically visualize protein distribution within the cell, genetic fusion to fluorescent protein (FP) has been a powerful strategy. The large mass of the FP component and their restricted spectra limit their application, however. Site specific post-translational labeling is an emerging complementary technology (see O'Hare et al., 17 Curr. Opin. Struct. Biol. 488-94 (2007)). One such approach is based on the enzymology of phosphopantetheinyl transferases (PPTases), either holo-(acyl carrier protein) synthase (AcpS) or Sfp. AcpS transfers the phosphopantetheinyl (Ppant) moiety from CoA to a conserved serine residue in the acyl carrier protein (ACP). This enzyme tolerates a wide range of modifications at the terminal thiol of CoA, allowing the transfer of a broad spectrum of fluorophores to an ACP on a tagged protein. Recent progress allows for the replacement of an ACP with 12-amino-acid-tag (A1) or even 8-amino-acid-tags (e.g., A-4 peptide, amino acid sequence DSLDMLEW; (SEQ ID NO: 1); Zhou et al., 2 ACS Chem. Bio. 337-46 (2007); Zhou et al., 130 J. Am. Chem. Soc. 9925-30 (2008)). PPTase labeling enables membrane proteins to be tracked with "built-in" high temporal and spatial resolution, with a minimal shift in molecular mass and a growing library of bright, photostable fluorophores that act across the visible spectrum. Because the time of labeling can be controlled precisely in the living cell, and the labeling reaction is rapid (typically completed within 15 to 30 minutes), multicolor pulse-chase experiments are facilitated by this approach. Further, PPTase specifically labels the extracellular component of cell membrane-bound proteins; consequently, surface and intracellular pools of a given membrane protein can be distinguished in the living cell.

An embodiment of the present invention used a Smo::FP fusion, in conjunction with AcpS labeling, to examine Smo distribution in response to a number of small molecule modulators of Hh pathway activity. Alternative dual labeling constructs include EGFP::Smo and Inversin::tagRFPT. Several Hh agonists and one antagonist, cyclopamine, stimulate the accumulation of Smo in the primary cilium of cultured cells. In contrast, other antagonists inhibit Shh-mediated Smo translocation to the primary cilium. Using AcpS labeling with a 12-amino-acid-tag (A1), provides evidence that most cilial localized Smo originates from intracellular protein pools and not from the cell membrane. The colocalization of IFT88, an anterograde IFT protein, with intracellular Smo suggests that Smo may traffic through an IFT mediated pathway.

The present invention has pharmacological implications for the different inhibitory mechanisms of cyclopamine and other antagonists. Understanding the normal cellular functions and properties of drug targets and how these are influenced by a drug is critical to both the development and the successful clinical application of a drug. "Mechanism-based" drug discovery, where drug development efforts are directed by identifying and better understanding the mechanisms by which drugs and their targets function, promises to increase the efficiency of drug development and to better address safety issues (Gibbs, 287 Science 1969-73 (2000)). Hh signaling is one critical pathway of interest based on its roles in both development and diseases. From many screens, Smo has emerged as the target for a majority of known compounds that modulate Hh signaling. Consequently, Smo has assumed an importance in pharmacological development of Hh agonists and antagonists.

Figure 3:
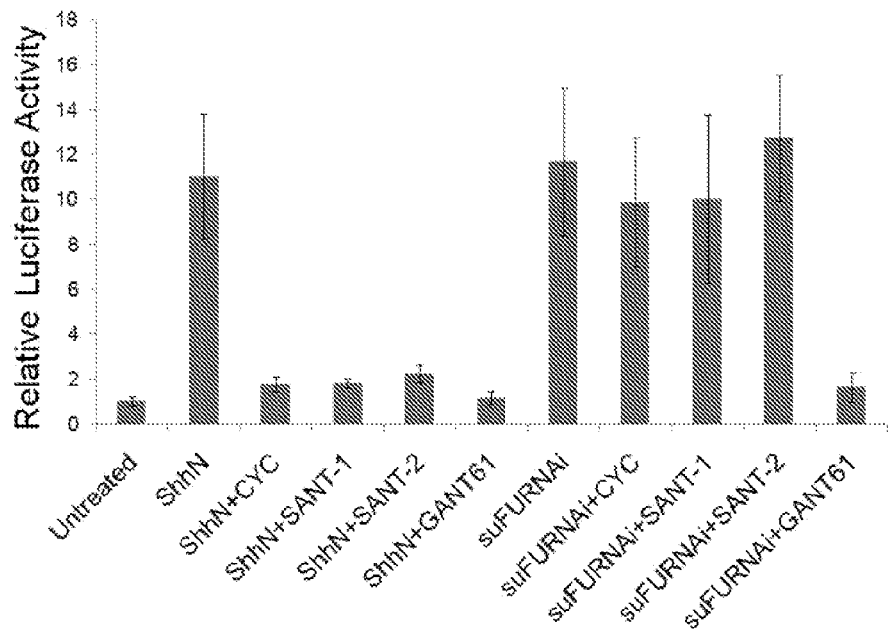
FIG. 3 shows the effects on Hh activity by various Hh agonists and antagonists. Hh signaling was activated by either ShhN ligand or RNAi knock down of suFU and assessed in Gli-luciferase assays. NIH/3T3 cells were either untreated or treated with one of the Hh antagonists, either CYC, SANT-1, SANT-2 or GANT61. The result shown is the mean of four replicates. Error bars depict SD.
Figure 6:
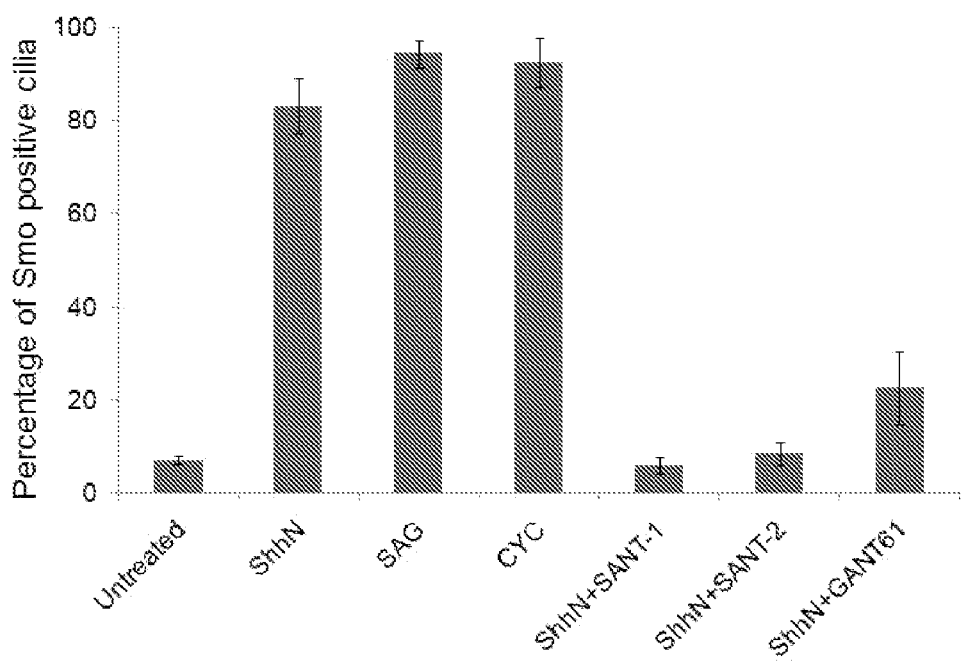
FIG. 6 presents the percentage of A1::Smo::GFP positive cilia after treatment with ShhN, SAG, CYC (cyclopamine), ShhN plus SANT-1, ShhN plus SANT-2, and ShhN plus GANT61. For each treatment, three fields containing 100-200 cells were randomly sampled and colocalization of GFP and Arl13b were scored to calculate the percentage of A1::Smo::GFP positive cilia. Bars denote the mean of data from three images. Error bars depict SD.
Figure 7:
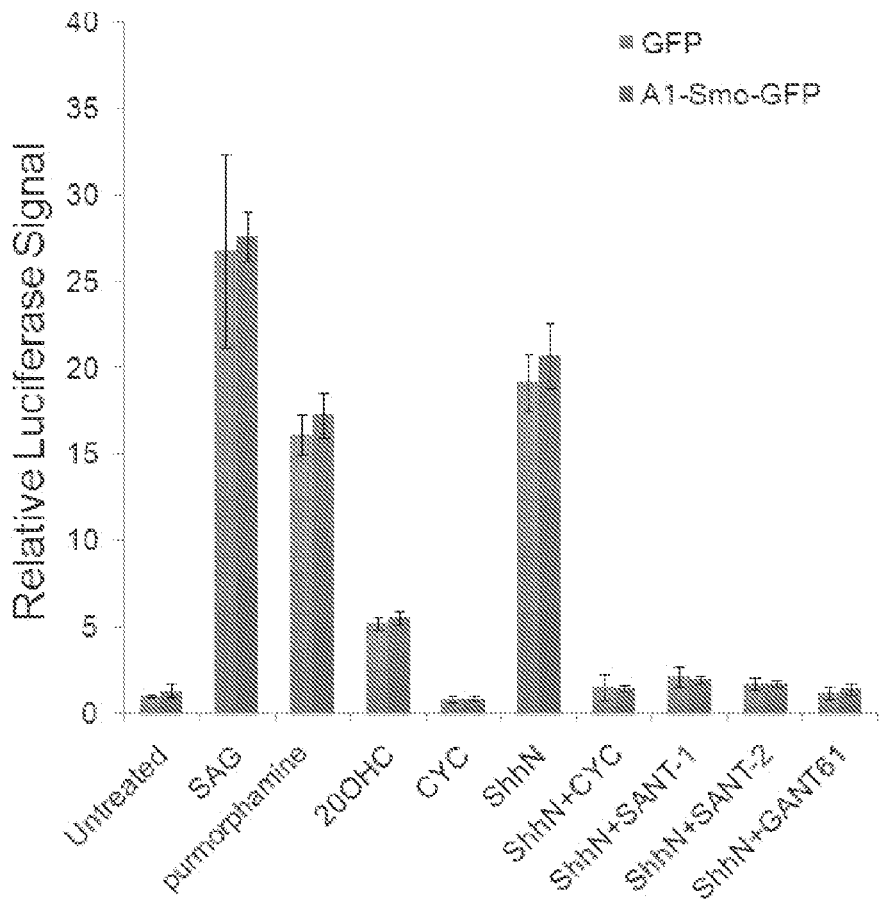
FIG. 7 compares the bioactivity of small molecule agonists and antagonists of Hh signaling. Gli luciferase assays were performed in A1::Smo::GFP producing cells (dark gray bars) and a control cell line that only produces GFP (light gray bars). Cells were either untreated or treated with SAG, ShhN, ShhN plus SANT-1, ShhN plus SANT-2, and ShhN plus GANT61, respectively. Data shown is the mean of 4 replicates. Error bars depict SD.

Herein, evidence is provided indicating that cyclopamine, SANT-1, SANT-2, and GANT61 have different effects on Smo translocation to the primary cilium (FIG. 3 and FIG. 6). SANT-1/2 have been suggested to act at the same level as cyclopamine because they compete with cyclopamine for binding to Smo (Chen et al., 2002). SANT-1/2 inhibit a dominant active form of Smo (SmoA1) at a comparable dose to that required to inhibit wild-type Smo (id.), although cyclopamine has to be applied at a much higher dose to block SmoA1 activity (Taipale et al., 2000). Because SANT-1/2 block Smo accumulation at the primary cilium while cyclopamine triggers translocation, and SANT-1/2 are chemically distinct compounds from cyclopamine (FIG. 9), their binding to Smo may occur at different sites, and their binding may induce different conformational changes in Smo protein and/or differentially disrupt Smo interaction with other cellular factors.

GANT61 functions downstream of Smo and suFU in the inhibition of Shh signaling (FIG. 3). As GANT61 inhibits Gli1 binding to DNA (Lauth et al., 2007), GANT61 may function at the level of Gli factors modulating their transcriptional activities. Three models may explain the unexpected inhibitory effect we observe of GANT61 on cilial accumulation of Smo. First, Smo accumulation to the primary cilium may be dependent on active Hh signaling. Second, normal feedback mechanisms may influence Smo cilial translocation. Transcription of Ptch1, Hip1, Cdo, Boc and Gas1 are all either positively or negatively regulated by Shh signaling, and altered levels of these components may indirectly effect Smo cilial translocation. Finally, GANT61 may target cilial trafficking more generally. As Gli processing and Smo accumulation are both dependent on the primary cilium, both processes could be influenced by a cilial trafficking defect. It has been reported, however, that GANT61 can act on nuclear accumulated Gli, which contradicts this model (Lauth et al., 2007).

Cyclopamine is one of the most widely used Hh antagonists in Hh-cancer research. Prolonged systemic treatment with cyclopamine is reported to significantly diminish tumor formation in UV-irradiated Ptch1$^{+/-}$ mice (Athar et al., 64 Cancer Res. 7545-52 (2004)). Cyclopamine can also decrease the rate of growth of mouse medulloblastoma cells both in culture and in mouse allograft models (Dahmane et al., 128 Devel. 5201-12 (2001); Berman et al., 297 Science 1559-61 (2002)). The finding herein that cyclopamine promotes Smo accumulation at the primary cilium suggests a possible issue with cyclopamine action where the Smo that has accumulated in the primary cilium may lead to a strong, prolonged stimulation after drug removal. Once in the primary cilium, Smo turns over relatively slowly. These results may have important ramifications in deciding which drugs to promote for clinical development and in ensuring the maximal 'target space' for Hh pathway inhibition.

Aspects of the present invention shed light on Smo trafficking and the intraflagellar transport (IFT) pathway. The data suggest that the primary mechanism for Smo accumulation at the primary cilium is via transport from an intracellular store. The finding that Smo and IFT88 co-localize in cytoplasmic accumulations and in the primary cilium provides some evidence for a trafficking process that could move Smo to the primary cilium. Seen in this light, mouse mutants in IFT proteins may have complicated roles in Hh signaling where both cilial structure and Smo transport may be affected. More specific mutants may be required to examine the possibility of distinct, mechanistic activities. Studies exploring the dynamic interactions between Smo, IFT88 and other components of the IFT pathway, shed light on their cellular relationships in conjunction with cilial cycling. Moreover, studying the pre-stimulation Smo complex may give insights into the mechanisms that activate Smo movement from the cytoplasm to the primary cilium. Recently, it was shown that suFU also depends on IFT (Ocbina & Anderson, 237 Devel. Dyn. 2030-38 (2008)). Given the cilial localization of several major components in the Hh pathway, examining the broad relationships between IFT proteins and Hh pathway components may be of interest. Future developments, such as orthogonal labeling with two different PPTases, Sfp and AcpS, may enhance the simultaneous investigation of multiple proteins (Zhou et al., 2007), and the development of additional cell permeable substrates may expand this important methodology for additional molecular imaging studies.

Figure 1B:
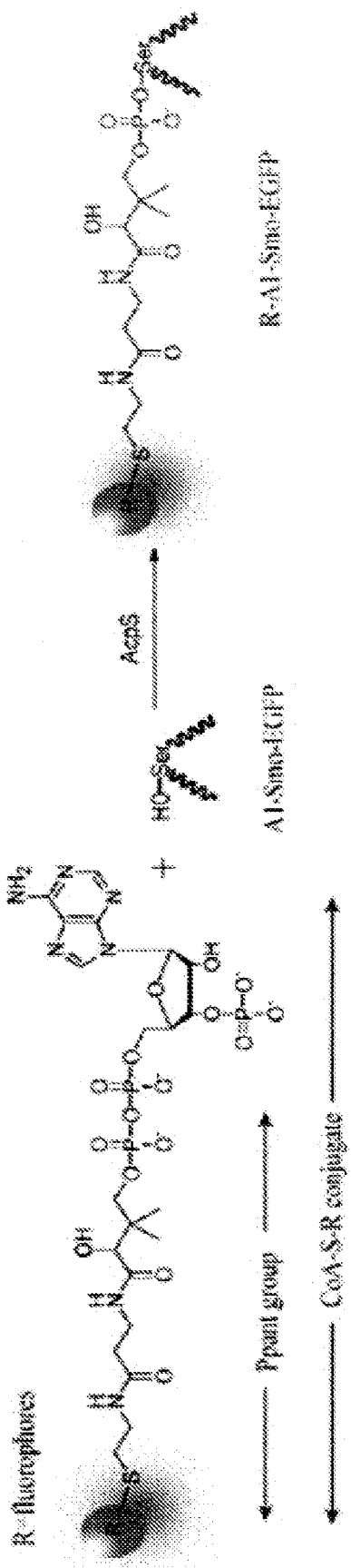

An aspect of the present invention provides for a A1::Smo::GFP construct that is functionally equivalent to endogenous Smo. This system allows the investigation of Smo localization and its trafficking mechanism, by combining conventional labeling with fluorescent proteins and a PPTase labeling technique (FIG. 1). GFP was fused to the intracellular C-terminus of human Smo and a 12 amino acid A1 tag was added at the extracellular N-terminus following the signal peptide sequence (FIG. 1A). The A1 peptide tag is recognized specifically by the AcpS enzyme. Enzymatic activity transfers a Ppant group in the CoA substrate to a serine residue in the A1 tag (FIG. 1B), thereby enabling fluorescent labeling of A1::Smo::GFP using CoA substrates conjugated with small fluorophores such as Texas Red (TxRed).

The A1::Smo::GFP or a control GFP constructs can be introduced into target cells by a number of known approaches. For example, the constructs were introduced into Shh-responsive NIH/3T3 cells by retroviral infection. Multiple clonal lines of A1::Smo::GFP expressing cells were selected based on the expression level and translocation behavior of A1::Smo::GFP. At least two clonal lines were used to validate the results throughout this study. In the absence of Shh ligand, endogenous Smo has a diffuse distribution in cells. Following treatment with ShhN (the N-terminal signaling fragment of Shh), Smo translocates to the primary cilium above the γ-tubulin-positive, basal body. A1::Smo::GFP fusion proteins showed a similar ShhN-dependent distribution to endogenous mouse Smo when they were detected with both GFP and Smo antibody (Rohatgi et al., 2007; Corbit et al., 2005; Han et al., 2008; Kiprilov et al., 2008; Kovacs et al., 2008; May et al., 2005; Tran et al., 2008). Cilial accumulation of A1::Smo::GFP in response to ShhN treatment was confirmed by co-staining with two additional primary cilium markers: anti-Arl13b and Inversin::Cherry. Arl13b is a GTPase required for proper cilia formation (Caspary et al., 2007), whereas Inversin is linked to the Wnt signaling pathway (Watanabe et al., 130 Devel. 1725-34 (2003)).

Figure 2:
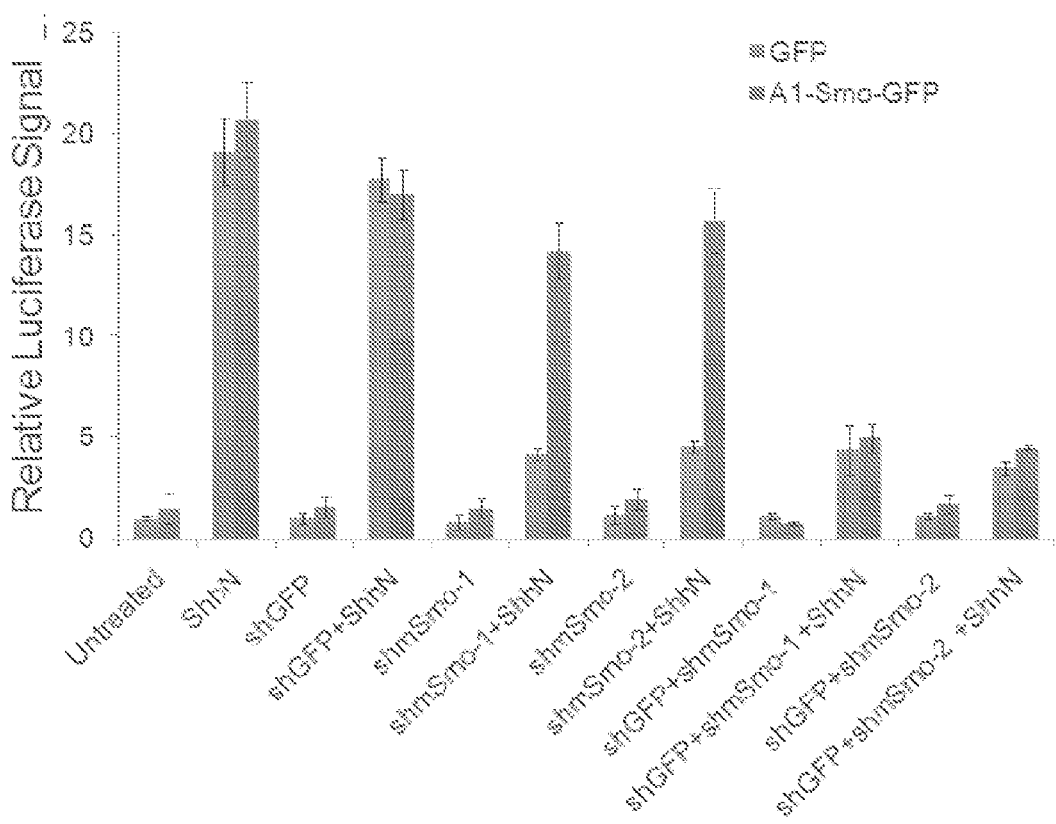
FIG. 2 shows A1::Smo::GFP is functionally equivalent to endogenous Smo. Hh signaling was assessed in NIH/3T3 cells by activation of a Ptch1-promoter driven luciferase reporter in response to ShhN ligand. Cells either expressed GFP (light bars) or A1::Smo::GFP (dark bars), and in some samples they were transfected with short hairpin (sh) RNA constructs to knock down GFP (shGFP) and/or endogenous mouse Smo (shmSmo-1 and shmSmo-2; recognizing non-overlapping regions specific to mouse and not human Smo). The result shown is the mean of four replicates. Error bars indicate SD. Color versions of these figures are shown in Wang et al., P.N.A.S. USA (2009).
Figure 5:
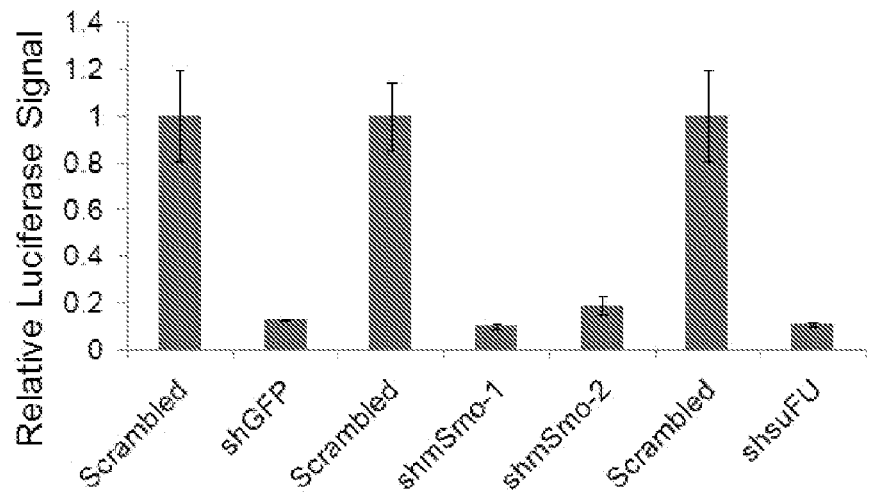
FIG. 5 depicts the measurements of knock-down efficiency by short hairpin RNA (shRNA) constructs recognizing GFP, Smo, and suFU target RNAs. A fusion construct between firefly luciferase and the shRNA target protein was co-transfected with a shRNA construct. A shRNA construct with scrambled sequence was transfected in an equal amount to establish the control level of luciferase signal without knock-down (shown as 1 in the bar graph). Data were normalized against *Renilla* luciferase. Data shown is the mean of four replicates. Error bars depict SD.

The functionality of the A1::Smo::GFP construct in Hh signaling was addressed in Gli-luciferase assays, using Gli-dependent transcription activity as a readout (FIG. 2). An equal amount of a Ptch1-promoter driven luciferase reporter construct was introduced into either A1::Smo::GFP cells or a control cell line producing GFP only. Co-transfection of short hairpin (sh) RNA constructs against GFP and mouse Smo was used to knock down A1::Smo::GFP and endogenous Smo, respectively, in transfected cells (FIG. 5) (Varjosalo et al., 10 Devel. Cell 177-86 (2006); Yu & McMahon, 44 Genesis 252-61 (2006)). Cells were serum-starved to promote cilial assembly, then treated with ShhN ligand or mock medium. A1::Smo::GFP cells were equally responsive to ShhN as the control cell line, whereas knockdown of GFP did not significantly attenuate ShhN responsiveness. As expected, knockdown of mouse Smo dramatically inhibited ShhN responsiveness of the control GFP cell line, but not the A1::Smo::GFP cell line (FIG. 2). Knockdown of both GFP and endogenous Smo, however, dramatically inhibited ShhN responsiveness in A1::Smo::GFP cells (FIG. 2). Together, these data demonstrate that A1::Smo::GFP is equivalent to endogenous Smo in terms of both its translocation behavior in response to ShhN ligand and Hh signaling activity in ShhN treated cells.

Different classes of agonists and antagonists differentially influence Smo localization. The localization of Smo to that of the general, primary cilium marker, Arl13b, was compared when cells were treated with a range of compounds that modulate Hh signaling (see FIG. 9). Consistent with a previous report (Rohatgi et al., 2007), Smo translocated to the primary cilium when NIH/3T3 cells were treated with SAG, 20-OHC or a third pathway agonist, purmorphamine. Surprisingly, cyclopamine, a widely used Hh antagonist, also drove Smo to the primary cilium, in contrast to a previous examination in MDCK cells (Corbit et al., 2005).

Conversely, other antagonists including SANT-1, SANT-2 and GANT61 abrogate the ShhN-dependent translocation of Smo to the primary cilium (FIG. 6), whereas they do not induce obvious localization change of Smo when applied alone. Similar results were obtained in an A1::Smo::GFP/Inversin::Cherry cell line, where primary cilia were labeled with an Inversin::Cherry fusion protein (Watanabe et al., 2003)). Because the cilial localization of Inversin::Cherry was unaltered by any of the treatments, the observed effects of Hh agonists and antagonists on A1::Smo::GFP cilial translocation were deemed specific and not a more general effect of altered cilial king. Importantly, Gli-luciferase reporter assays demonstrated that all small molecule treatments produced the expected effects on Hh signaling activity when compared to their published properties (Rubin & de Sauvage, 2006; Bijlsma, et al., 2006; Chen et al., 2002; Corcoran & Scott, 2006; Frank-Kamenetsky et al., 2002; Lauth et al., 2007; Rohatgi et al., 2007; Sinha & Chen, 2006; Williams et al., 2003.

How these different antagonists function in the Hh pathway was determined using an epistasis analysis in NIH/3T3 cells. All four compounds inhibited ShhN-stimulated Hh activity, but only GANT61 inhibited Gli activity when the endogenous Gli antagonist suFU was knocked down (FIG. 3) (Cooper et al., 132 Devel. 4407-17 (2005); Svard et al., 10 Devel. Cell 187-97 (2006)). These data agree with published reports (Chen et al., 2002; Lauth et al., 2007). SANT-1 and SANT-2 function upstream of suFU, most likely at the level of Smo because they both compete for cyclopamine binding of Smo (Chen et al., 2002). In contrast, the GANT61 function downstream of suFU places GANT61 at the level of Gli transcriptional regulators (Lauth et al., 2007).

The inventive system presented herein showed that cilial accumulation of Smo originates from an intracellular source. More specifically, the cellular source of Smo that accumulates on the primary cilium was explored utilizing PPTase labeling technology. AcpS enzyme and CoA substrates were added to the culture medium to label A1::Smo::GFP in living cells. As the high, negative charge of the CoA substrates prevents their penetration through the cell membrane, only A1::Smo::GFP on the cell surface can be labeled by this approach (Zhou et al., 2007, Zhou et al., 2008). Thus, A1::Smo::GFP can be distinguished in cell membrane and intracellular pools.

Figure 4:
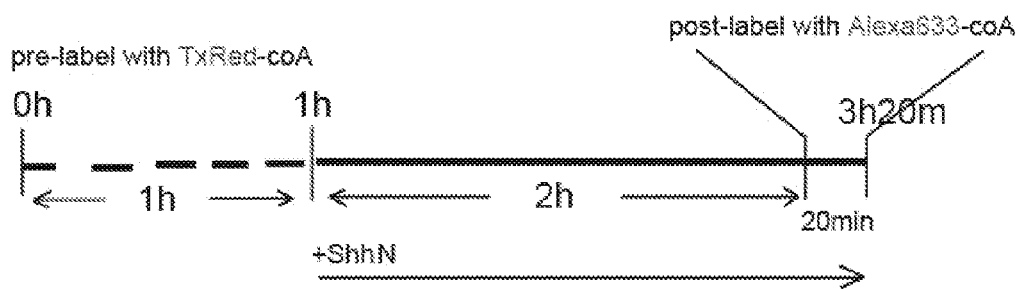
FIG. 4 is a schematic to demonstrate AcpS labeling of A1::Smo::GFP. using an experimental procedure for a 'pulse-chase' labeling with two colors.
Figure 8:
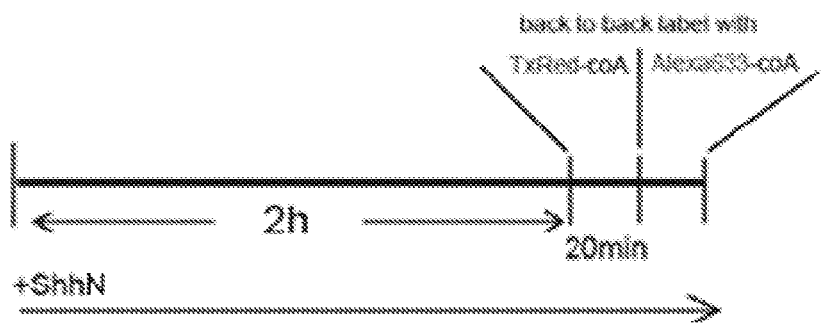
FIG. 8 diagrams a protocol for a 20-minute AcpS labeling that saturates A1 sites on the primary cilium. Cells expressing A1::Smo::GFP were treated with ShhN for 2 hours, followed by two consecutive labeling reactions with TxRed-CoA and Alexa633-CoA, respectively.
Figure 10:
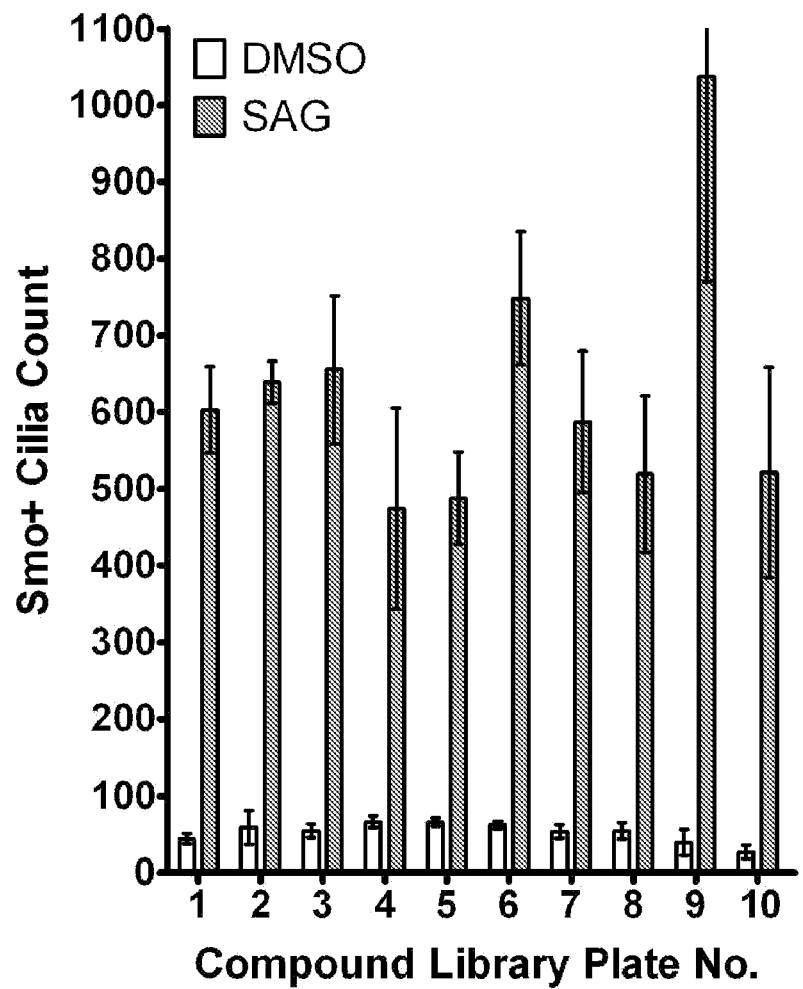
FIG. 10 shows a Smo translocation high content screen. The data measurement is the count of Smo::GFP positive cilia in each well. DMSO was used as an unstimulated negative control and SAG, a Smo agonist, was used as a positive control. Each data point show the mean and standard deviation from six replicates with the same compound (numeral) plate as indicated.

AcpS labeling efficiency was examined with two different fluorophores: TxRed and Alexa633. After ShhN stimulated accumulation of A1::Smo::GFP, a 20-minute labeling reaction was performed with two CoA substrates conjugated with either TxRed or Alexa633. A1::Smo::GFP was effectively labeled with both fluorophores in a reaction dependent on both AcpS and A1 tag. Next, A1::Smo::GFP cells were grown in conditions that stimulate de novo assembly of the primary cilium (Examples, below). Unstimulated cells were incubated for 1 hour with AcpS enzyme and TxRed-CoA to saturate labeling of A1::Smo::GFP on the membrane surface. Following this, cells were treated with ShhN ligand for 2 hours and labeled with Alexa633-CoA (FIG. 4). A1::Smo::GFP on the primary cilium was only labeled by Alexa633. To confirm that cell surface labeling was indeed saturated after 1-hour incubation, ShhN-treated cells were incubated consecutively with two different fluorescent substrates, for 20 minutes each (FIG. 8). Labeling was only observed with the first fluorophore, consistent with a rapid saturation of available A1 tag sites in the first reaction. The data suggest that the A1::Smo::GFP that translocates to the primary cilium on ShhN stimulation originates primarily from an intracellular pool and not from the cell membrane.

One possible caveat to this interpretation is the kinetics of turn-over of A1::Smo::GFP: A1::Smo::GFP could rapidly translocate from the cell membrane to the primary cilium but then turn over at this site within the 2-hour assay period. Hence, to explore A1::Smo::GFP turn-over in the primary cilium, cells were treated with ShhN ligand for 2 hours, then labeled with TxRed for 20 minutes, to directly observe cilial protein at different periods post-labeling. No obvious decrease in signal intensity was observed 2 hours post labeling. Additionally, label was still detected on the primary cilium 8 hours after labeling. Together, these data support the conclusion that intracellular trafficking from a cytoplasmic pool is primarily responsible for the elevation of Smo levels at the primary cilium following ShhN stimulation. Because SAG and cyclopamine treatments gave similar results, this pathway is also the likely route for small-molecule driven Smo relocalization.

Interestingly, Smo likely traffics through an intraflagellar transport (IFT) pathway. The potential pathways of Smo trafficking to the primary cilium were examined by assaying cytoplasmic co-localization of Smo with vesicle trafficking pathways on ShhN stimulation. Non-cilial associated, cytoplasmic accumulations of A1::Smo::GFP in response to ShhN ligand was observed. Further, some A1::Smo::GFP puncta colocalized with endogenous IFT88 (Polaris), an anterograde IFT protein (Haycraft et al., 2005), raising the possibility that Smo might traffic through an IFT mechanism. These puncta, unlike cilial A1::Smo::GFP, were not labeled by AcpS indicating that the non-cilial IFT88 associated accumulations did not originate from the cell surface. Further, the bulk of A1::Smo::GFP did not colocalize with Transferin receptors (TfR), a general marker for endocytosis (van Dam & Stoorvogel, 13 Mol. Biol. Cell 169-82 (2002)); EEA-1, an early endosome marker (FIG. 13B) (Perez-Victoria et al., 19 Mol. Biol. Cell 2350-62 (2008)); or mannose 6 phosphate receptor (M6PR), a marker for late endosomes and lysosomes (Perez-Victoria et al., 2008). Together, these data contradict an endosomal pathway of membrane translocation. Recently, a BBSome complex has been linked to membrane vesicle trafficking to the base of the primary cilium (Nachury et al., 129 Cell 1201-13 (2007)). A1::Smo::GFP did not co-localize with PCM-1, a key component of BBSome complex, however. Thus, Smo is also unlikely to traffic through the BBSome pathway (Nachury et al., 129 Cell 1201-13 (2007); Dammermann & Merdes, 159 J. Cell Biol. 255-66 (2002).

EXAMPLES

Example 1

Assays for Smo Translocation

All 3T3 cell lines were plated at a density of $1 \times 10^4$ cells per well in fibronectin coated Lab-Tek™ Chamber Slides (Nunc, 178599). The cells were grown to confluence, then switched to DMSO containing 0.5% BCS with indicated treatments for 24 hr or as stated elsewhere herein. Immunostaining was performed after fixation in 4% Paraformaldehyde (PFA) according to standard protocols. AcpS labeling reactions were performed as described previously (Zhou et al., 2007). Fluorescent images were collected after fixing samples using a Zeiss LSM510 META on an inverted microscope, with a 63× (1.4 NA) oil-immersion objective lens utilizing four laser lines (405 nm, 488 nm, 543 nm, 633 nm).

Example 2

Luciferase Assays

Cells were plated at a density of 5×10$^4$ per well in 24-well plates 18 hr prior to transfection. DNA transfection was performed using Lipofectamine™ 2000 transfection reagent (Invitrogen, #11668); the DNA introduced in each well included 100 ng CMV driven *Renilla* luciferase construct, 300 ng Ptch1 promoter-driven firefly luciferase construct, and 400 ng of each shRNA construct or a PBS plasmid as a control. Cells were grown for two days; then the medium was changed to DMEM containing 0.5% BCS and proteins/compounds indicated in the text. Cells were cultured for an additional 48 hr, tryspinized, lysed and assayed using a Promega Dual Luciferase Reporter Essay System Kit (E1910). *Renilla* luciferase signal was used to normalize the firefly luciferase signal. The RNAi efficiency was measured as previous described (Varjosalo et al., 2006). In all luciferase assays, every condition was repeated in quadruplicate wells and experiments were repeated at least three times.

Example 3

Constructs and Cell Lines

Enhanced GFP (EGFP) and monomeric Cherry (mCherry) were subcloned separately into pBabe-Puro and pBabe-Neo constructs (Addgene) (Morgenstern & Land, 18 Nucleic Acids Res. 1068 (1990)), to generate pBabe-GFP and pBabe-Cherry constructs. Human Smo was amplified by PCR with the A1 tag (amino acid sequence: GDSLDMLEWSLM (SEQ ID NO: 2)) at the N-terminus and subcloned into the pBabe-GFP construct. Mouse Inversin was amplified from an Inversin::CFP construct (Stanford Univ., Palo Alto, Calif.) and subcloned into the pBabe-Cherry construct.

shRNA constructs for RNAi knockdown experiments, as well as the GFP::luciferase, Smo::luciferase and suFU::luciferase constructs employed here to determine the efficiency of traffic RNAi action, have been reported elsewhere (Varjosalo et al., 10 Devel. Cell 177-86 (2006); Yu & McMahon, 44 Genesis 252-61 (2006)). The target sequences for RNAi constructs are as follows: shGFP: gcaagctgaccctgaagttcat (SEQ ID NO: 3); shmSmo-1: ccgagcagatggcaccatgag (SEQ ID NO: 4); shmSmo-2: aagccaacatg tggctggttg (SEQ ID NO: 5); shsuFU: cgatatgtcttccagtcagag (SEQ ID NO: 6). (Smo and suFU from National Public Health Institute, Helsinki, Finland).

NIH/3T3 cells (American Tissue Culture Collection, ATCC) were maintained in DMEM supplemented with 10% bovine calf serum (BCS). HEK293 cells (ATCC) were maintained in DMEM supplemented with 10% fetal bovine serum (FBS). Retroviruses were produced by transfecting HEK293 cells with pBabe constructs and a packaging construct (pCL-Eco, Addgene). To generate GFP and A1::Smo::GFP cell lines, NIH/3T3 cells were separately infected by retroviruses containing pBabe-GFP and pBabe-A1::Smo::GFP constructs. Cells were split into new plates at a dilution of 1:200 and maintained in the selective medium containing 1 μg/ml puromycin (Sigma-Aldrich, #P9620) until colonies formed. Monoclonal colonies were picked and expanded. Each clone was examined for the translocation behavior of the A1::Smo::GFP construct in response to ShhN and SAG treatments and its expression level. Clones that showed low level expression and expected ShhN translocation behavior were selected for further study. GFP cell clones with a similar level of protein were selected as control lines. A1::Smo::GFP/Inversin::Cherry cell lines were generated by infecting A1::Smo::GFP cell lines with retrovirus containing pBabe-Inversin::Cherry. G418 (Invitrogen, #11811) was applied at 0.8 mg/ml to select Inversin::Cherry positive clones.

Example 4

Antibodies and Reagents

Rabbit anti-Smo antibody (Rohatgi et al., 317 Science 372-76 (2007)), was used at a dilution of 1:500. Rabbit anti-Arl13b (Caspary et al., 12 Devel. Cell 767-78 (2007)) (Emory Univ., Atlanta, Ga.), was used at a dilution of 1:1,000. Rabbit anti-IFT88 (Haycraft, et al., 1 PLoS Genet. e53 (2005)) (Univ. Alabama, Birmingham, Ala.), was used at a dilution of 1:2, 000. Rabbit anti-PCM-1 (Dammermann & Merdes, 159 J. Cell Biol. 255-66 (2002)) (CNRS-Pierre Fabre, France), was used at a dilution of 1:500. Mouse anti-acetylated tubulin (#T7451; Sigma-Aldrich, St. Louis, Mo.) was used at a dilution of 1:2,500. Mouse anti-gamma-tubulin (#T6557, Sigma-Aldrich), rabbit anti-gamma-tubulin (#T5192, Sigma-Aldrich), and rabbit anti M6PR (Abcam, ab2733) were all used at a dilution of 1:1,000. Mouse anti-EEA-1 (BD Biosciences, Palo Alto, Calif., No. 610456) was used at dilution of 1:500. Rat anti-TfR (eBioscience, #14-0711) was used at a dilution of 1:100. Alexa405, Alexa568, and Alexa633 conjugated secondary antibodies (Invitrogen) were used at a dilution of 1:500.

Mouse recombinant ShhN purified protein was purchased from R&D Systems (#464-SH-025). SAG, SANT-2, and GANT61 were purchased from Axxora (#ALX-270-426, #ALX-270-436, #ALX-270-482; Axxora, LLC, San Diego, Calif.). SANT-1 was obtained from Tocris Bioscience (#1974). DMSO was from Sigma Aldrich (D2650). Purmorphamine was from Calbiochem (#540220). The working concentrations of these reagents in this study are as following: ShhN was applied at 25 nM; SAG was applied at 200 nM; purmorphamine, 20-OHC, cyclopamine, and GANT61 were applied at 10 μM; SANT-1 and SANT-2 were applied at 1 μM. AcpS, Texas Red-CoA, and Alexa633-CoA were prepared as described previously (Zhou et al., 130 J. Am. Chem. Soc. 9925-30 (2008)).

Example 5

High Throughput Screening of Smo Cilial Translocation Agonists

Chemical libraries were constructed in 384-well format. A1::Smo::GFP cells were plated in 384-well plates and cultured for three days or until confluent. Upon serum starvation, chemicals were added to cells in three different concentrations. The cell were stained and fixed, and the chemical intracellular translocation effects characterized by automatic imaging and data analysis (OPERA™ high content screening system, Perkin Elmer Inc., Waltham, Mass.).

Using this approach, about 5,700 biologically active compounds were screened for Smo cilial translocation. Approximately 160 compounds were scored as potential hits in the primary screen, and thereafter assayed in twelve doses for both Smo cilial translocation and Gli-luciferase. Of these 160 or so compounds, about 40 compounds were identified as Smo cilial translocation agonists.

Example 6

High Throughput Screening of Smo Cilial Translocation Antagonists

Chemical libraries were constructed in 384-well format. A1::Smo::GFP cells were plated in 384-well plates and cultured for three days or until confluent. Upon serum starvation, chemicals were added to cells in three different concentrations with ShhN-conditioned medium. The cells were stained and fixed, and the chemical intracellular translocation effects characterized by automatic imaging and data analysis.

Using this approach, about 8,600 biologically active compounds were screened for Smo cilial translocation. 316 compounds were scored as potential hits in the primary screen and thereafter assayed in twelve doses for both Smo cilial translocation and Gli-luciferase. Over 25 compounds were identified as potential Smo cilial translocation antagonists.

We claim:

1. A method for screening a drug affect on the Hedgehog (Hh) signaling pathway comprising the steps of:
   culturing a first population and second population of cells, wherein both populations express a A::Smoothened::Fluorescent Protein construct (A::Smo::FP), and wherein A is a fragment of an acyl carrier protein that suffices for post-translational phosphopantetheinylation of A::Smo::FP protein;
   labeling both the first and second cell populations with a fluorophore using AcpS;
   contacting the first cell population with a Hh ligand;
   contacting the second cell population with a Hh ligand and a drug;
   observing the cilial translocation of said A::Smo::FP in the first cell population and in the second cell population by visualizing the FP and fluorophore;
   comparing the cilial translocation of said A::Smo::FP in the first cell population with the second cell population;
   wherein a difference in cilial translocation of said A::Smo::FP in the first cell population and the second cell population provides an indication of whether said drug affects the Hh signaling pathway.

2. The method of claim 1, wherein said FP is Green Fluorescent Protein (GFP) or Yellow Fluorescent Protein (YFP).

3. The method of claim 1, wherein A is peptide A1, having the amino acid sequence GDSLDMLEWSLM (SEQ ID NO: 2).

4. The method of claim 1, wherein A is peptide A-4, having the amino acid sequence DSLDMLEW (SEQ ID NO: 1).

5. The method of claim 1, wherein the observing and comparing steps are automated.

6. A method for high throughput screening for Hh antagonists or agonists using the method of claim 1.

7. A method for investigating the response of a cell membrane protein in a living cell to a drug comprising:
   (a) identifying a cell membrane protein for investigation, wherein said membrane protein responds to a stimulus by translocation;
   (b) obtaining a gene that expresses a recombinant version of said membrane protein;
   (c) creating a genetic construct that adds (i) at least one acyl carrier protein peptide tag to the membrane-associated portion of said membrane protein and (ii) at least one visual marker to said recombinant protein, wherein said construct is expressed in a cell as a chimeric membrane protein;
   (d) introducing said construct into a cell such that said chimeric membrane protein is expressed;
   (e) labeling the membrane portion of said chimeric membrane protein with a fluorophore via AcpS;
   (f) contacting said cell with a drug;
   (g) observing translocation activity of said chimeric membrane protein within said cell by observing the fluorophore and the visual marker of the chimeric membrane protein;
   wherein an effect of the drug on translocation activity of the chimeric membrane protein indicates whether the drug is an antagonist, agonist, or does not affect translocation of said cell membrane protein.

8. The method of claim 7, wherein said visual marker is GFP.

9. The method of claim 7, wherein said acyl carrier protein peptide tag is A1.

10. The method of claim 7, wherein said fluorophore is Texas red and the visual marker is GFP.

11. The method of claim 7, wherein said construct is A1::Smo::GFP.

12. The method of claim 7, wherein said introducing step uses a retroviral vector.

13. The method of claim 7, wherein said contacting and observing is automated.

14. A cell culture system comprising a population of cells that expresses a reporter construct comprising A::Smo::FP, and wherein A is a fragment of an acyl carrier protein that suffices for post-translational phosphopantetheinylation in a living cell, Smo is Smoothened protein, and FP is a fluorescent protein.

15. A method of identifying a drug that affects a Hh signaling pathway comprising contacting a cell culture system of claim 14 with a candidate drug and detecting an effect on the reporter construct as compared with a culture system not contacted with the drug, wherein a difference is indicative of a drug that affects a Hh signaling pathway.

* * * * *

UNITED STATES PATENT AND TRADEMARK OFFICE
CERTIFICATE OF CORRECTION

PATENT NO.        : 8,574,837 B2                                      Page 1 of 1
APPLICATION NO. : 13/142438
DATED             : November 5, 2013
INVENTOR(S)       : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 229 days.

Signed and Sealed this
Twenty-second Day of September, 2015

Michelle K. Lee
*Director of the United States Patent and Trademark Office*

```
SEQUENCE LISTING

<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Ser Leu Asp Met Leu Glu Trp
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Asp Ser Leu Asp Met Leu Glu Trp Ser Leu Met
1               5                   10

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcaagctgac cctgaagttc at                                              22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccgagcagat ggcaccatga g                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
aagccaacat gtggctggtt g                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgatatgtct tccagtcaga g                                             21
```